United States Patent [19]
Sykes et al.

[11] Patent Number: 5,573,764
[45] Date of Patent: Nov. 12, 1996

[54] USE OF INTERLEUKIN-12 TO PREVENT GRAFT VERSUS HOST DISEASE

[75] Inventors: Megan Sykes, Charlestown; Stanley F. Wolf, Arlington, both of Mass.

[73] Assignees: Genetics Institute, Inc., Cambridge; The General Hospital Corporation, Boston, both of Mass.

[21] Appl. No.: 186,529

[22] Filed: Jan. 21, 1994

[51] Int. Cl.$^6$ ................................................ A61K 45/05
[52] U.S. Cl. .......................................... 424/85.2; 514/21
[58] Field of Search .............................. 424/85.2; 514/21

[56] References Cited

FOREIGN PATENT DOCUMENTS

| | | |
|---|---|---|
| 0625354A1 | 4/1994 | European Pat. Off. |
| WO93/17698 | 9/1993 | WIPO |

OTHER PUBLICATIONS

Gaddy, J. et al., J. Immunol. 150:96A (1993).
Azuma, E. et al., J. Immunol. 143:1524–1529 (1989).
Klimpel, G. et al., J. Immunol. 144:84–93 (1990).
Niederwieser, D. et al., Transplantation 50:620–625 (1990).
Troutt, A. et al., PNAS 89:5276–5280 (1992).
Mowat, A., Immunology 68:18–23 (1989).
Allen, R. et al., Eur. J. Immunol. 23:333–337 (1993).
Brok, H. P. M. et al., J. Immunol. 151:6451–6459 (1993).
Jadus, M. et al., Bone Marrow Transplant 10:1–14 (1992).
Antin, J. et al., Blood 80:2964–2968 (1992).
Dickinson, A. et al., Bone Marrow Transplant 7:209–216 (1991).
Parkman, R. et al., J. Cell Biochem. 16(a):186 (1992).
Thiele, D. et al., J. Immunol. 138:51–57 (1987).
Piguet, P. et al., J. Exp. Med. 166:1280–1289 (1987).
Holler, E. et al., Blood 75:1011–1016 (1990).
Holler, E. et al., Transplant Proc. 25:1234–1236 (1993).
Shalaby, M. et al., Transplantation 47:1057–1061 (1989).
Cesano et al., Progress in Clinical and Biological Research 389: 165–173 (1994).
Via et al., Arthritis and Rheumatism, 36(9):263 (1993).
Soiffer et al., Blood 82(9):2790–2796 (1993).
Sykes et al., J. Exp. Med., vol. 171, pp. 645–658 1990.
Sykes et al., PNAS, vol. 87, pp. 5633–5637, 1990.
Sykes et al., J. Immunol., vol. 150(1), pp. 197–205, Jan. 1993.
Azuma et al., J. Immunol., vol. 143(5), pp. 1524–1529, Sep. 1989.
Gately et al., Cell. Immunol., vol. 143, pp. 127–142, 1992.
Soiffer et al., Blood, vol. 82(9), pp. 2790–2796, Nov. 1993.
Jacobsen et al., J. Exp. Med., vol. 178, pp. 413–418, Aug. 1993.
Chau et al., J. Exp. Med. vol. 173, pp. 869–879, 1991.
The Enconomist, "Panic in the Petri Dish", pp. 61–62, Jul. 1994.
Cross et al., Infection and Immunity, vol. 61(7), pp. 2741–2747, Jul. 1993.
Osband et al., Immunology Today, vol. 11 (6), pp. 193–195, 1990.
Waldmann et al., Science, vol. 252, pp. 1657–1662, Jun. 1991.

*Primary Examiner*—Chhaya D. Sayala
*Attorney, Agent, or Firm*—Scott A. Brown; Thomas J. DesRosier

[57] ABSTRACT

The use of interleukin-12 to prevent, to ameliorate, and to treat graft-versus-host disease in a mammal in need of such treatment is disclosed.

10 Claims, No Drawings

USE OF INTERLEUKIN-12 TO PREVENT GRAFT VERSUS HOST DISEASE

This invention was made with Government support under Grant Nos. AI-31158, CA-55290, HL-49915, CA-55553 and HL-48049 awarded by the National Institutes of Health. As a result, the Government may have certain rights in this invention.

BACKGROUND OF THE INVENTION

The present invention relates to the field of prevention and treatment of graft-versus-host disease using interleukin-12.

An individual mammal's immune system functions through recognition of certain cell surface proteins, some of which are termed major histocompatibility complex proteins, or MHC proteins. Additional minor histocompatibility proteins exist which can also contribute to immunological recognition events, The individual mammal's immune system recognizes its own MHC proteins, or those of its identical twin, as self and thus does not destroy its own cells or those of its identical twin. Members of the same species may share major and/or minor histocompatibility antigens, and thus an individual may not recognize the cells of another member of its species as non-self, depending on the degree of the differences between the MHC proteins of the two individuals. When an individual's immune system recognizes the cells of other members of the same species as non-self, the first individual's immune system may proceed to destroy the cells of the second individual. In humans, the major histocompatibility proteins are known as "HLA" antigens.

When tissues such as bone marrow, blood cells, or solid organs are transplanted from one individual to another, normally the recipient will recognize the donor's cells as non-self and the recipient's immune system will destroy the donor's cells as described above. For this reason, in a tissue transplantation, the recipient is normally subjected to immunosuppressive drugs and/or irradiation. However, transplantation patients are also subject to immunologic recognition in the opposite direction, that is, the donor tissue may contain immunologically competent cells which proceed to destroy the recipient's cells, a condition termed "graft-versus-host disease" or "GVHD".

At the present time, many leukemia and lymphoma patients are treated by bone marrow transplantation. When an identical twin is available, such transplantation is termed "syngeneic" since the genetic characteristics of donor and recipient are identical. More frequently, bone marrow transplantations are "allogeneic", that is, the bone marrow which is transplanted is donated by an individual whose genetic characteristics differ from those of the recipient, especially as regards the MHC and minor histocompatibility antigens expressed on the surfaces of each individual's cells. Allogeneic bone marrow transplantation is being performed more and more frequently. In 1990, more than 4,000 such transplantations occurred. In recognition of the increasing need for bone marrow donors compatible with potential recipients, an international marrow donor registration system has been developed, in order to provide phenotypically matched marrow from unrelated donors.

Concomitant with the increasing frequency of allogeneic bone marrow transplantation, the incidence of potentially fatal complications such as graft-versus-host disease is also increasing. Graft-versus-host disease can develop when bone marrow, blood products, or solid organs containing immunocompetent cells are transferred from a donor to a recipient. Thus, when MHC antigenic differences exist between the donor and recipient, the recipient is at risk for the development of graft-versus-host disease. Graft-versus-host disease may also develop when there are antigenic differences between donor and recipient for the minor histocompatibility antigens. Thus, graft-versus-host disease can also develop between MHC-matched persons. Moreover, surgery patients who receive directed blood transfusion, for example, transfusion of blood from an HLA homozygous child to a heterozygous parent, may also develop graft-versus-host disease.

Presently graft-versus-host disease is inhibited by attempting to eliminate immunocompetent donor cells, for example, by in vitro manipulation of the donor bone marrow. For example, immunocompetent T cells may be removed from the donor bone marrow through physical separation such as by lectin agglutination, or by treatment of the bone marrow with monoclonal antibodies directed to T cells. However, use of bone marrow depleted of T cells is associated with a higher rate of graft failure, which is frequently fatal. Use of T cell depleted bone marrow grafts is also associated with an increased incidence of relapse among the recipients, particularly recipients having chronic myelocytic leukemia.

In another approach, the recipient is subjected to immunosuppressive therapy after transplantation. Such immunosuppression may occur by use of glucocorticoids, cyclosporin, methotrexate, or combinations of such drugs. However, immunosuppression results in increased incidence of infection, and even when immunosuppressant drugs are used, graft-versus-host disease may still occur.

Interleukin-12 is a heterodimeric cytokine which was originally identified as a factor which induces γ-interferon from T cells and natural killer cells as set forth in PCT/US91/06332, published Apr. 2, 1992, which is incorporated herein by reference. PCT/US91/06332 refers to interleukin-12 as Natural Killer Cell Stimulating Factor or NKSF. EP 433827, published Jun. 26, 1991 discloses interleukin-12 as a cytotoxic lymphocyte maturation factor (CLMF). The amino acid sequences of the human interleukin-12 subunits are set forth in SEQ ID NO: 1/SEQ ID NO: 2 (40 kD subunit) and SEQ ID NO: 3/SEQ ID NO: 4 (35 kD subunit).

Interleukin-12 also stimulates natural killer cells in vitro by increasing their ability to lyse target cells at a level comparable to that obtained with interferon-α and interleukin-2, well-known activators of natural killer cells' cytotoxic activity. Additional in vitro activities of interleukin-12 which have been identified include induction of T cell proliferation as a co-stimulant; suppression of interleukin-2 induced proliferation of natural killer blasts; suppression of interleukin-2 induced proliferation of T cell receptor-γδ-positive cells; promotion of Th1 T cell differentiation from progenitors; enhancement of Th1, but not Th2 proliferation; enhancement of T cell cytolytic activity; enhancement of cytotoxic lymphocyte generation; enhancement of natural killer and natural killer blast cytolytic activity; ex vivo enhancement of natural killer activity in peripheral blood mononuclear cells of interleukin-2-treated patients; induction of adhesion molecules on natural killer cells; induction of perforin and granzyme B mRNAs in natural killer blasts; induction of interleukin-2 receptor subunits (p55, p75) on natural killer cells; induction of low levels of tumor necrosis factor-α; suppression of IgE synthesis by interferon-γ-dependent and independent mechanisms; modulation of T cell development in fetal thymic organ cultures; and synergy with kit ligand to promote growth of myeloid and B cell progenitors. The known in vivo activities of interleukin-12 include induction of interferon-γ; enhancement of natural killer cell activity in spleen, liver, lungs and peritoneal cavity; enhancement of generation of allo-specific cytotoxic lymphocytes; induction of extramedullary hematopoiesis in mouse spleen; reversible suppression of hematopoiesis in bone marrow; reversible induction of anemia, lymphopenia, and neutropenia in mice; suppression of anti-IgD induced IgE, IgG1, and interleukin-4 expression; increased survival in SCID mice treated with *Toxoplasma gondii;* cure of leishmaniasis in susceptible strains of mice; decreased bioburden in cryptococcoses model; suppression of tumor growth; and promotion of immunity to tumor cells. Interleukin-12 is also induced in vivo in the shwarzman reaction model of septic shock.

From the known activities of interleukin-12, it would be expected that treatment of mammals in allogeneic bone marrow transplantation would result in more severe graft-versus-host disease. Both interferon-γ and tumor necrosis factor-α, which are induced by interleukin-12 treatment, have been implicated in producing graft-versus-host disease. Furthermore, cytotoxic T-lymphocytes, whose generation is enhanced by interleukin-12, have also been implicated in graft-versus-host disease pathophysiology. Murine studies have shown that inhibition of a Th1 response by treatment with interleukin-2 is associated with inhibition of graft-versus-host disease. Therefore, enhancement of Th1 responses by treatment with interleukin-12 would be expected to increase the severity of graft-versus-host disease.

SUMMARY OF THE INVENTION

In one embodiment, the invention comprises a method of preventing graft-versus-host disease which comprises administering to a mammal, at the time of bone marrow transplantation, a therapeutically effective amount of interleukin-12.

In another embodiment, the invention comprises a method of ameliorating graft-versus-host disease which comprises administering to a mammal, at the time of bone marrow transplantation, a therapeutically effective amount of interleukin-12.

In yet another embodiment, the invention comprises a method of treating graft-versus-host disease which comprises administering to a mammal experiencing graft-versus-host disease a therapeutically effective amount of interleukin-12.

DETAILED DESCRIPTION OF THE INVENTION

The present inventors have surprisingly found that treatment of mammals subjected to allogeneic bone marrow transplantation with interleukin-12, with or without co-administration of T-cell depleted syngeneic marrow, results in prolonged survival of said mammals, a result which indicates that interleukin-12 is useful for prevention of graft-versus-host disease in some cases and in amelioration of said disease in other cases. Specifically, as set forth in Example 1 below, mice which had been lethally irradiated and infused with bone marrow and spleen cells from fully MHC mismatched donor mice demonstrated prolonged survival from a course of interleukin-12 prophylaxis.

In accordance with the present invention, therefore, interleukin-12 is defined as a heterodimeric glycoprotein comprised of two covalently linked subunits, one of said subunits having a molecular weight of about 40 kD and being characterized by the amino acid sequence set forth in SEQ ID NO:1/SEQ ID NO:2, and the other subunit having a molecular weight of about 35 kD and being characterized by the amino acid sequence set forth in SEQ ID NO:3/SEQ ID NO:4. Any form of interleukin-12 may be used as a component of the pharmaceutical composition used to practice the method of the invention, so long as that form of interleukin-12 is capable of preventing, ameliorating, or treating graft-versus-host disease in a mammal at risk for that disease. For example, interleukin-12 may be in the form of the heterodimer comprised of a 40 kD subunit disulfide-bonded to a 35 kD subunit. When interleukin-12 is a heterodimer, the 40 kD subunit has substantial homology to the 40 kD subunit of human interleukin-12 as set forth in SEQ ID NO:1/SEQ ID NO: 2 and is disulfide bonded to a 35 kD subunit having substantial homology to the 35 kD subunit of human interleukin-12 as set forth in SEQ ID NO:3/SEQ ID NO:4. "Substantial homology" means greater than 75% homology at the amino acid level, while retaining the ability to preventing, ameliorating, or treating graft-versus-host disease in a mammal at risk for that disease. Another form of interleukin-12 which may be used in the present invention is an interleukin-12 subunit capable of preventing, ameliorating, or treating graft-versus-host disease in a mammal at risk for that disease. Such an interleukin-12 40 kD subunit has substantial homology to the human interleukin-12 40 kD subunit of SEQ ID NO:1/SEQ ID NO:2, and such an interleukin-12 35 kD subunit has substantial homology to the human interleukin-12 35 kD subunit of SEQ ID NO:3/SEQ ID NO:4. Fragments of the interleukin-12 subunits that retain interleukin-12 biological activity are also be useful to prevent or treat graft-versus-host disease in a mammal at risk for that disease, in accordance with the present invention.

For use in the present invention, it is preferable to produce interleukin-12 recombinantly, through expression of DNA sequences encoding one or both of the interleukin-12 subunits in a suitable transformed host cell. For example, using known methods the DNA sequences encoding human interleukin-12 set forth in SEQ ID NO:1 (40 kD subunit) and SEQ ID NO:3 (35 kD subunit) may be linked to an expression vector such as pED (Kaufman et al., Nucleic Acids Res. 19, 4484–4490(1991)). In such an expression vector, sequences which optimize translation such as CCACC (Kozak, M., Nucleic Acids Res. 12, 857–871 (1984)) may be added 5' to the initiation codon using known methods. The expression vector containing the interleukin-12 subunits may then be transformed into a host cell, and protein expression may be induced and maximized, to produce heterodimeric human interleukin-12. For production of heterodimeric interleukin-12,the DNA sequences encoding the interleukin-12 subunits may be present on different expression plasmids or present in tandem on a single expression plasmid.

When a subunit or fragment of interleukin-12 is used to practice the present invention, it may also be produced recombinantly using known methods. For example, the DNA sequence encoding the human interleukin-12 40 kD subunit set forth in SEQ ID NO:1 may be linked to an expression vector, transformed into a host cell, and expression induced and maximized to produce the human interleukin-12 40 kD subunit. Similiarly, the DNA sequences encoding the human interleukin-12 35 kD subunit as set forth in SEQ ID NO:3 may be linked to an expression vector, transformed into a host cell, and expression induced and maximized to produce the corresponding protein. Of course, degenerate DNA sequences encoding the interleukin-12 subunits may also be employed to produce interleukin-12 for use in the present invention, as can DNA sequences encoding allelic variants of the interleukin-12 subunits.

Any suitable expression vector may be employed to produce interleukin-12 for use in the present invention. For mammalian expression, numerous expression vectors are known in addition to the pED vector mentioned above, such as pEF-BOS (Mizushima et al., Nucleic Acids Res. 18, 5322 (1990)); pXM, pJL3 and pJL4 (Gough et al., EMBO J. 4, 645–653 (1985)); and pMT2 (derived from pMT2-VWF, A.T.C.C. #67122; see PCT/US87/00033). Suitable expression vectors for use in yeast, insect, and bacterial cells are also known. Construction and use of such expression vectors is well within the level of skill in the art.

Suitable host cells for recombinant production of interleukin-12 useful in the present invention include, for example, mammalian cells such as Chinese hamster ovary (CHO) cells, monkey COS cells, mouse 3T3 cells, mouse L cells, myeloma cells such as NSO (Galfre and Milstein, Methods in Enzymology 73, 3–46 (1981)), baby hamster kidney cells, and the like. Interleukin-12 may also be produced by transformation of yeast, insect, and bacterial cells with DNA sequences encoding the interleukin-12 subunits, induction and amplification of protein expression, using known methods.

Recombinantly produced interleukin-12 can be purified from culture medium or cell extracts by conventional purification techniques. Culture medium or cell extracts containing interleukin-12 may be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylamioethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. The purification of interleukin-12 from culture supernatant may also include one or more column steps over such affinity resins as lectin-agarose, heparin-toyopearl® or Cibacrom blue 3GA Sepharose®; or by hydrophobic interaction chromatography using such resins as phenyl ether, butyl ether, or propyl ether; or by immunoaffinity chromatography. Finally, one or more reverse-phase high performance liquid chromatography (RP-HPLC) steps employing hydrophobic RP-HPLC media, e.g., silica gel having pendant methyl or other aliphatic groups, can be employed to further purify interleukin-12 for use in the present methods and compositions. Some or all of the foregoing purification steps, in various combinations, can be employed to provide a substantially homogeneous isolated recombinant protein. Purification of interleukin-12 subunits or fragments for use in the present invention may differ from the optimal protocol for purification of the heterodimeric protein.

Preferably, when human interleukin-12 is produced recombinantly as set forth above, it may be purified by the following method. The cells in which the human interleukin-12 has been made may be removed from the conditioned medium by filtration, and the conditioned medium is loaded onto Q-Sepharose FastFlow™ (available from Pharmacia) or an equivalent anion exchange medium, which has been equilibrated in 10-30 mMTris-HCl, pH 7.8–8.3. The column is then washed extensively with the same buffer followed by a wash with 30–45mM histidine, pH 5.1–5.8, followed by a wash with the original equilibration buffer. The recombinant human interleukin-12 is eluted from the column with a buffer containing 20–50mMTris-HCl, pH 7.8–8.5, and 0.15 to 0.50M NaCl. The eluted material is loaded onto CM-Sepharose FastFlow™ (available from Pharmacia) or equivalent cation exchange medium which has been equilibrated in 20–50 mM MES, pH 5.7–6.4, and washed extensively with the same buffer. The column is washed with a buffer containing 20–40 mM sodium phosphate, pH 6.8–7.5 and 0.2–0.5M NaCl. The eluted material is concentrated using an Amicon™ S1Y30 or equivalent spiral cartridge membrane which has been washed and equilibrated in the elution buffer used in the CM-Sepharose FastFlow™ column. The material is concentrated to approximately 5% of the column volume of the final chromatographic step, which is size exclusion using S200 Sephacryl™ (available from Pharmacia) or an equivalent size exclusion resin. The size exclusion column is equilibrated and eluted with phosphate buffered saline, pH 7.2–7, and the recombinant human interleukin-12 peak is collected and filtered for use in the method of the invention. Those of skill in the art of protein purification may use alternative purification methods to obtain recombinantly-produced human interleukin-12 for use in the method of the invention.

Interleukin-12 may be purified from culture medium or extracts of cells which naturally produce the protein and used in the present invention. Exemplary purification schemes for naturally produced interleukin-12 are set forth in PCT/US91/06332 and in EP 433827.

For use in the method of the invention, a therapeutically effective amount of interleukin-12 is administered to a mammal at risk of developing graft-versus-host disease. As used herein, the term therapeutically effective amount means the total amount of each active component of the pharmaceutical composition or method that is sufficient to show a meaningful patient benefit, i.e., a reduction in the incidence or severity of acute or chronic graft-versus-host disease compared to that expected for a comparable group of patients not receiving interleukin-12, as determined by the attending physician. When applied to an individual active ingredient administered alone, the term refers to that ingredient alone. When applied to a combination, the term refers to combined amounts of the active ingredients that result in the therapeutic effect, whether administered in combination, serially, or simultaneously.

In practicing the method of the present invention, a therapeutically effective amount of interleukin-12 is administered to a mammal at risk of developing graft-versus-host disease. The interleukin-12 may be administered in accordance with the method of the invention either alone or in combination with other therapies such as treatments employing T cell-depleted autologous or syngeneic bone marrow, immunosuppressive drugs, cytokines, lymphokines, or other hematopoietic factors.

When co-administered with T-cell-depleted autologous or syngeneic bone marrow, immunosuppressive drugs, one or more cytokines, lymphokines, or other hematopoietic factors, the interleukin-12 may be administered either simultaneously with the T-cell-depleted autologous or syngeneic bone marrow, immunosuppressive drugs, cytokine(s), lymphokine(s), other hematopoietic factor(s), for sequentially. If administered sequentially, the attending physician will decide on the appropriate sequence of administering the interleukin-12 in combination with the T-cell depleted autologous or syngeneic bone marrow, immunosuppressive drugs, cytokine(s), lymphokine(s), and other hematopoietic factor(s).

Administration of the interleukin-12 used to practice the method of the present invention can be carried out in a variety of conventional ways, such as oral ingestion, inhalation, or cutaneous, subcutaneous, or intravenous injection. Intravenous or subcutaneous administration to the patient is preferred.

When a therapeutically effective amount of interleukin-12 is administered orally, the interleukin-12 will be in the form of a tablet, capsule, powder, solution or elixir. When administered in tablet form, the pharmaceutical composition of the invention may additionally contain a solid carrier such as a gelatin or an adjuvant. The tablet, capsule and powder contain from about five to 95% interleukin-12, preferably from about 25–90% interleukin-12. When administered in liquid form, a liquid carrier such as water, petroleum, oils of animal or plant origins such as peanut oil, mineral oil, soy bean oil, or sesame oil, or synthetic oils, may be added. The liquid form of the pharmaceutical composition may further contain physiological saline solution, dextrose, or other saccharide solutions, or glycols such as ethylene glycol, propylene glycol or polyethylene glycol. When administered in liquid form, the pharmaceutical composition contains about 0.5 to 90% by weight of interleukin-12 and preferably from about i to 50% interleukin-12.

When a therapeutically effective amount of interleukin-12 is administered by intravenous, cutaneous or subcutaneous injection, the interleukin-12 will be in the form a pyrogen-free, parenterally-acceptable aqueous solution. The preparation of such parenterally-acceptable protein solutions, having due regard to pH, isotonicity, stability, and the like, is within the skill in the art. A preferred pharmaceutical composition for intravenous, cutaneous, or subcutaneous injection should contain, in addition to interleukin-12, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition for use in the present method may also contain stabilizers, preservatives, buffers, antioxidants, or other additive known to those with skill in the art. It is contemplated that the pharmaceutical composition used to practice the method of the present invention should contain about 0.1 pg to about 100 mg of interleukin-12 per ml of solution, preferably about 0.1 mg of interleukin-12 per ml of solution.

In practicing the method of preventing or ameliorating graft-versus-host disease in accordance with the present invention, it is contemplated that the duration of the application of interleukin-12 will be in the range of 12–48 hours of continuous or intermittent subcutaneous or intravenous administration, beginning at the time of transplantation. For the purpose of the present invention, "at the time of bone marrow transplantation" is defined as being during the 1 hour period before or the 1 to 24 hour period after the bone marrow transplantation. As an example of a method for preventing or ameliorating graft-versus-host disease, preferably 1 ng/kg to 100 µg/kg of interleukin-12 may be administered daily to the mammal, more preferably 5 ng/kg to 10 µg/kg of interleukin-12 may be administered daily to the mammal, and most preferably 10 ng/kg to 1 µg/kg may be administered daily to the mammal. In one preferred dosage regimen, the first dose of interleukin-12 is given one hour after bone marrow transplantation and two more doses are given on days one and two post-transplant. Alternative treatment regimens may be appropriate for individual patients and will be determined by the attending physician, taking into account the nature and severity of the condition being treated, and the nature of the prior treatments which the patient has undergone.

Modifications of the treatment regimen set forth above for prevention or ameliorating graft-versus-host disease may be made for treatment of ongoing acute or chronic graft-versus-host disease. For the purpose of the present invention, "acute graft-versus-host disease" is defined as occurring during the time period from three days to 100 days post transplantation in humans or from three days to 30 days post transplantation in mice; and "chronic graft-versus-host disease" is defined as occurring at any time after 100 days post-transplantation in humans or at any time after 30 days post transplantation in mice. As an example of a method for treating ongoing acute or chronic graft-versus-host disease, 1 pg/kg to 100 µg/kg may be administered daily to a mammal experiencing acute or chronic graft-versus-host disease, until improvement or remission of the symptoms of acute or chronic graft-versus-host disease is observed. Ultimately, the attending physician will decide on the appropriate duration of subcutaneous or intravenous therapy using the pharmaceutical composition of interleukin-12 in the method of the present invention.

EXAMPLE 1

Use of Recombinant Murine IL-12 for the Inhibition of Graft-Versus-Host Disease (GVHD) in Mice Thirty C57B1/10 mice were lethally irradiated with 10.25 Gy whole body irradiation. On the same day, 27 of these mice received an intravenous inoculum containing $9 \times 10^6$ bone marrow cells and $13 \times 10^6$ spleen cells (as an additional source of GVHD-causing T lymphocytes) from fully MHC-mismatched (and multiple minor histocompatibility antigen-mismatched) A/J donor mice. In addition, 18 of these mice received $5 \times 10^6$ B10 (i.e., host-type syngeneic, the murine counterpart of autologous marrow) T cell-depleted (TCD) bone marrow cells in the same inoculum. The three remaining mice served as non-GVHD controls, and received T cell-depleted B10 marrow only.

Nine of the 18 mice receiving A/J bone marrow and spleen cells plus TCD B10 BMC were treated with recombinant murine interleukin-12 (Schoenhaut et al., J. Immunol. 148, 3433–3440 (1992)) at a dose of 1 µg (approximately 50 µg/kg) per day intraperitoneally on days 0, 1, and 2 (day 0 being the day of the transplant). In addition, the group receiving A/J bone marrow and spleen cells alone also received a similar course of interleukin-12 prophylaxis.

The result of this experiment was that most of the mice (8 of 9) receiving A/J bone marrow and spleen cells plus TCD B10 bone marrow cells died by day 10. The death was due to GVHD, as recipients of TCD syngeneic marrow alone all survived in excellent health. In the interleukin-12-treated group that also received A/J bone marrow and spleen cells plus TCD B10 bone marrow cells, none of the nine animals died by day 10, and all were still alive by day 20. This protective effect of interleukin-12 was somewhat dependent on the co-administration of TCD B10 bone marrow cells, since 5 of 9 animals receiving A/J bone marrow and spleen cells without TCD B10 BMC, plus interleukin-12 treatment, died by day 9. Thus, interleukin-12 protected against acute GVHD mortality, and this effect was most marked when TCD host-type bone marrow cells were also given. In a second experiment, animals receiving interleukin-12 prophylaxis against graft-versus-host disease induced by A/J bone marrow and spleen cells showed similar graft-versus-host disease protection, both in the presence and in the absence of T-cell-depleted host-type bone marrow.

What is claimed is:

1. A method of preventing graft-versus-host disease which comprises administering to a mammal, at the time of bone marrow transplantation, a therapeutically effective amount of interleukin-12.

2. The method of claim 1, wherein the therapeutically effective amount of interleukin-12 comprises 1 to 100 µg/kg body weight.

3. The method of claim 2, wherein the interleukin-12 is administered for three days beginning on the day of the bone marrow transplant.

4. A method of ameliorating graft-versus-host disease which comprises administering to a mammal, at the time of bone marrow transplantation, a therapeutically effective amount of interleukin-12.

5. The method of claim 4, wherein the therapeutically effective amount of interleukin-12 comprises 1 ng to 100 µg/kg body weight.

6. The method of claim 5, wherein the interleukin-12 is administered for three days beginning on the day of the bone marrow transplant.

7. A method of treating graft-versus-host disease which comprises administering to a mammal experiencing graft-versus-host disease a therapeutically effective amount of interleukin-12.

8. The method of claim 7, wherein the therapeutically effective amount of interleukin-12 comprises 1 to 100 µg/kg body weight.

9. The method of claim 8, wherein the interleukin-12 is administered daily until improvement of the acute graft-versus-host disease is observed.

10. The method of claim 8, wherein the interleukin-12 is administered daily until remission of the graft-versus-host disease is observed.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 987 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens
        ( G ) CELL TYPE: Lymphoblast
        ( H ) CELL LINE: RPMI 8866

( i x ) FEATURE:
        ( A ) NAME/KEY: CDS
        ( B ) LOCATION: 1..987

( x i ) SEQUENCE DESCRIPTION: SEQ ID NO:1:

```
ATG TGT CAC CAG CAG TTG GTC ATC TCT TGG TTT TCC CTG GTT TTT CTG    48
Met Cys His Gln Gln Leu Val Ile Ser Trp Phe Ser Leu Val Phe Leu
 1               5                  10                  15

GCA TCT CCC CTC GTG GCC ATA TGG GAA CTG AAG AAA GAT GTT TAT GTC    96
Ala Ser Pro Leu Val Ala Ile Trp Glu Leu Lys Lys Asp Val Tyr Val
            20                  25                  30

GTA GAA TTG GAT TGG TAT CCG GAT GCC CCT GGA GAA ATG GTG GTC CTC   144
Val Glu Leu Asp Trp Tyr Pro Asp Ala Pro Gly Glu Met Val Val Leu
        35                  40                  45

ACC TGT GAC ACC CCT GAA GAA GAT GGT ATC ACC TGG ACC TTG GAC CAG   192
Thr Cys Asp Thr Pro Glu Glu Asp Gly Ile Thr Trp Thr Leu Asp Gln
    50                  55                  60

AGC AGT GAG GTC TTA GGC TCT GGC AAA ACC CTG ACC ATC CAA GTC AAA   240
Ser Ser Glu Val Leu Gly Ser Gly Lys Thr Leu Thr Ile Gln Val Lys
 65                 70                  75                  80

GAG TTT GGA GAT GCT GGC CAG TAC ACC TGT CAC AAA GGA GGC GAG GTT   288
Glu Phe Gly Asp Ala Gly Gln Tyr Thr Cys His Lys Gly Gly Glu Val
                85                  90                  95

CTA AGC CAT TCG CTC CTG CTG CTT CAC AAA AAG GAA GAT GGA ATT TGG   336
Leu Ser His Ser Leu Leu Leu Leu His Lys Lys Glu Asp Gly Ile Trp
            100                 105                 110

TCC ACT GAT ATT TTA AAG GAC CAG AAA GAA CCC AAA AAT AAG ACC TTT   384
Ser Thr Asp Ile Leu Lys Asp Gln Lys Glu Pro Lys Asn Lys Thr Phe
        115                 120                 125

CTA AGA TGC GAG GCC AAG AAT TAT TCT GGA CGT TTC ACC TGC TGG TGG   432
Leu Arg Cys Glu Ala Lys Asn Tyr Ser Gly Arg Phe Thr Cys Trp Trp
    130                 135                 140

CTG ACG ACA ATC AGT ACT GAT TTG ACA TTC AGT GTC AAA AGC AGC AGA   480
Leu Thr Thr Ile Ser Thr Asp Leu Thr Phe Ser Val Lys Ser Ser Arg
145                 150                 155                 160

GGC TCT TCT GAC CCC CAA GGG GTG ACG TGC GGA GCT GCT ACA CTC TCT   528
Gly Ser Ser Asp Pro Gln Gly Val Thr Cys Gly Ala Ala Thr Leu Ser
                165                 170                 175

GCA GAG AGA GTC AGA GGG GAC AAC AAG GAG TAT GAG TAC TCA GTG GAG   576
Ala Glu Arg Val Arg Gly Asp Asn Lys Glu Tyr Glu Tyr Ser Val Glu
            180                 185                 190

TGC CAG GAG GAC AGT GCC TGC CCA GCT GCT GAG GAG AGT CTG CCC ATT   624
Cys Gln Glu Asp Ser Ala Cys Pro Ala Ala Glu Glu Ser Leu Pro Ile
        195                 200                 205
```

```
GAG GTC ATG GTG GAT GCC GTT CAC AAG CTC AAG TAT GAA AAC TAC ACC      672
Glu Val Met Val Asp Ala Val His Lys Leu Lys Tyr Glu Asn Tyr Thr
    210             215                 220

AGC AGC TTC TTC ATC AGG GAC ATC ATC AAA CCT GAC CCA CCC AAG AAC      720
Ser Ser Phe Phe Ile Arg Asp Ile Ile Lys Pro Asp Pro Pro Lys Asn
225                 230                 235                 240

TTG CAG CTG AAG CCA TTA AAG AAT TCT CGG CAG GTG GAG GTC AGC TGG      768
Leu Gln Leu Lys Pro Leu Lys Asn Ser Arg Gln Val Glu Val Ser Trp
                245                 250                 255

GAG TAC CCT GAC ACC TGG AGT ACT CCA CAT TCC TAC TTC TCC CTG ACA      816
Glu Tyr Pro Asp Thr Trp Ser Thr Pro His Ser Tyr Phe Ser Leu Thr
            260                 265                 270

TTC TGC GTT CAG GTC CAG GGC AAG AGC AAG AGA GAA AAG AAA GAT AGA      864
Phe Cys Val Gln Val Gln Gly Lys Ser Lys Arg Glu Lys Lys Asp Arg
        275                 280                 285

GTC TTC ACG GAC AAG ACC TCA GCC ACG GTC ATC TGC CGC AAA AAT GCC      912
Val Phe Thr Asp Lys Thr Ser Ala Thr Val Ile Cys Arg Lys Asn Ala
    290                 295                 300

AGC ATT AGC GTG CGG GCC CAG GAC CGC TAC TAT AGC TCA TCT TGG AGC      960
Ser Ile Ser Val Arg Ala Gln Asp Arg Tyr Tyr Ser Ser Ser Trp Ser
305                 310                 315                 320

GAA TGG GCA TCT GTG CCC TGC AGT TAG                                  987
Glu Trp Ala Ser Val Pro Cys Ser
                325
```

(2) INFORMATION FOR SEQ ID NO:2:

(i) SEQUENCE CHARACTERISTICS:
        (A) LENGTH: 328 amino acids
        (B) TYPE: amino acid
        (D) TOPOLOGY: linear (ii) MOLECULE TYPE: protein (xi) SEQUENCE DESCRIPTION: SEQ ID NO:2:

```
Met Cys His Gln Gln Leu Val Ile Ser Trp Phe Ser Leu Val Phe Leu
 1               5                  10                  15

Ala Ser Pro Leu Val Ala Ile Trp Glu Leu Lys Lys Asp Val Tyr Val
                20                  25                  30

Val Glu Leu Asp Trp Tyr Pro Asp Ala Pro Gly Glu Met Val Val Leu
            35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
                100                 105                 110

Ser Thr Asp Ile Leu Lys Asp Gln Lys Glu Pro Lys Asn Lys Thr Phe
            115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190
```

| | | | | | | | | | | | | | | | |
|---|---|---|---|---|---|---|---|---|---|---|---|---|---|---|---|
|Cys|Gln|Glu<br>195|Asp|Ser|Ala|Cys|Pro<br>200|Ala|Ala|Glu|Glu|Ser<br>205|Leu|Pro|Ile|
|Glu|Val<br>210|Met|Val|Asp|Ala|Val<br>215|His|Lys|Leu|Lys|Tyr<br>220|Glu|Asn|Tyr|Thr|
|Ser<br>225|Ser|Phe|Phe|Ile|Arg<br>230|Asp|Ile|Ile|Lys|Pro<br>235|Asp|Pro|Pro|Lys|Asn<br>240|
|Leu|Gln|Leu|Lys|Pro<br>245|Leu|Lys|Asn|Ser|Arg<br>250|Gln|Val|Glu|Val|Ser<br>255|Trp|
|Glu|Tyr|Pro|Asp<br>260|Thr|Trp|Ser|Thr|Pro<br>265|His|Ser|Tyr|Phe|Ser<br>270|Leu|Thr|
|Phe|Cys|Val<br>275|Gln|Val|Gln|Gly|Lys<br>280|Ser|Lys|Arg|Glu|Lys<br>285|Lys|Asp|Arg|
|Val|Phe<br>290|Thr|Asp|Lys|Thr|Ser<br>295|Ala|Thr|Val|Ile|Cys<br>300|Arg|Lys|Asn|Ala|
|Ser<br>305|Ile|Ser|Val|Arg|Ala<br>310|Gln|Asp|Arg|Tyr|Tyr<br>315|Ser|Ser|Ser|Trp|Ser<br>320|
|Glu|Trp|Ala|Ser|Val<br>325|Pro|Cys|Ser| | | | | | | | |

( 2 ) INFORMATION FOR SEQ ID NO:3:

( i ) SEQUENCE CHARACTERISTICS:
        ( A ) LENGTH: 660 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens
        ( G ) CELL TYPE: Lymphoblast
        ( H ) CELL LINE: RPMI 8866

( i x ) FEATURE:
        ( A ) NAME/KEY: CDS
        ( B ) LOCATION: 1..660

( x i ) SEQUENCE DESCRIPTION: SEQ ID NO:3:

| | | | | | | | | | | | | | | | | |
|---|---|---|---|---|---|---|---|---|---|---|---|---|---|---|---|---|
|ATG|TGT|CCA|GCG|CGC|AGC|CTC|CTC|CTT|GTG|GCT|ACC|CTG|GTC|CTC|CTG|48|
|Met<br>1|Cys|Pro|Ala|Arg<br>5|Ser|Leu|Leu|Leu|Val<br>10|Ala|Thr|Leu|Val|Leu<br>15|Leu| |
|GAC|CAC|CTC|AGT|TTG|GCC|AGA|AAC|CTC|CCC|GTG|GCC|ACT|CCA|GAC|CCA|96|
|Asp|His|Leu|Ser<br>20|Leu|Ala|Arg|Asn|Leu<br>25|Pro|Val|Ala|Thr|Pro<br>30|Asp|Pro| |
|GGA|ATG|TTC|CCA|TGC|CTT|CAC|CAC|TCC|CAA|AAC|CTG|CTG|AGG|GCC|GTC|144|
|Gly|Met|Phe<br>35|Pro|Cys|Leu|His|His<br>40|Ser|Gln|Asn|Leu|Leu<br>45|Arg|Ala|Val| |
|AGC|AAC|ATG|CTC|CAG|AAG|GCC|AGA|CAA|ACT|CTA|GAA|TTT|TAC|CCT|TGC|192|
|Ser|Asn<br>50|Met|Leu|Gln|Lys|Ala<br>55|Arg|Gln|Thr|Leu|Glu<br>60|Phe|Tyr|Pro|Cys| |
|ACT|TCT|GAA|GAG|ATT|GAT|CAT|GAA|GAT|ATC|ACA|AAA|GAT|AAA|ACC|AGC|240|
|Thr<br>65|Ser|Glu|Glu|Ile|Asp<br>70|His|Glu|Asp|Ile|Thr<br>75|Lys|Asp|Lys|Thr|Ser<br>80| |
|ACA|GTG|GAG|GCC|TGT|TTA|CCA|TTG|GAA|TTA|ACC|AAG|AAT|GAG|AGT|TGC|288|
|Thr|Val|Glu|Ala|Cys<br>85|Leu|Pro|Leu|Glu|Leu<br>90|Thr|Lys|Asn|Glu|Ser<br>95|Cys| |
|CTA|AAT|TCC|AGA|GAG|ACC|TCT|TTC|ATA|ACT|AAT|GGG|AGT|TGC|CTG|GCC|336|
|Leu|Asn|Ser|Arg<br>100|Glu|Thr|Ser|Phe|Ile<br>105|Thr|Asn|Gly|Ser|Cys<br>110|Leu|Ala| |
|TCC|AGA|AAG|ACC|TCT|TTT|ATG|ATG|GCC|CTG|TGC|CTT|AGT|AGT|ATT|TAT|384|
|Ser|Arg|Lys|Thr|Ser<br>115|Phe|Met|Met|Ala|Leu<br>120|Cys|Leu|Ser|Ser|Ile<br>125|Tyr| |

|     | 115 |     |     |     |     | 120 |     |     |     |     | 125 |     |     |     |     |     |
| --- | --- | --- | --- | --- | --- | --- | --- | --- | --- | --- | --- | --- | --- | --- | --- | --- |
| GAA | GAC | TTG | AAG | ATG | TAC | CAG | GTG | GAG | TTC | AAG | ACC | ATG | AAT | GCA | AAG | 432 |
| Glu | Asp | Leu | Lys | Met | Tyr | Gln | Val | Glu | Phe | Lys | Thr | Met | Asn | Ala | Lys |     |
|     | 130 |     |     |     |     | 135 |     |     |     |     | 140 |     |     |     |     |     |
| CTT | CTG | ATG | GAT | CCT | AAG | AGG | CAG | ATC | TTT | CTA | GAT | CAA | AAC | ATG | CTG | 480 |
| Leu | Leu | Met | Asp | Pro | Lys | Arg | Gln | Ile | Phe | Leu | Asp | Gln | Asn | Met | Leu |     |
| 145 |     |     |     |     | 150 |     |     |     |     | 155 |     |     |     |     | 160 |     |
| GCA | GTT | ATT | GAT | GAG | CTG | ATG | CAG | GCC | CTG | AAT | TTC | AAC | AGT | GAG | ACT | 528 |
| Ala | Val | Ile | Asp | Glu | Leu | Met | Gln | Ala | Leu | Asn | Phe | Asn | Ser | Glu | Thr |     |
|     |     |     |     | 165 |     |     |     |     | 170 |     |     |     |     | 175 |     |     |
| GTG | CCA | CAA | AAA | TCC | TCC | CTT | GAA | GAA | CCG | GAT | TTT | TAT | AAA | ACT | AAA | 576 |
| Val | Pro | Gln | Lys | Ser | Ser | Leu | Glu | Glu | Pro | Asp | Phe | Tyr | Lys | Thr | Lys |     |
|     |     |     | 180 |     |     |     |     | 185 |     |     |     |     | 190 |     |     |     |
| ATC | AAG | CTC | TGC | ATA | CTT | CTT | CAT | GCT | TTC | AGA | ATT | CGG | GCA | GTG | ACT | 624 |
| Ile | Lys | Leu | Cys | Ile | Leu | Leu | His | Ala | Phe | Arg | Ile | Arg | Ala | Val | Thr |     |
|     |     | 195 |     |     |     |     | 200 |     |     |     |     | 205 |     |     |     |     |
| ATT | GAT | AGA | GTG | ATG | AGC | TAT | CTG | AAT | GCT | TCC | TAA |     |     |     |     | 660 |
| Ile | Asp | Arg | Val | Met | Ser | Tyr | Leu | Asn | Ala | Ser |     |     |     |     |     |     |
|     | 210 |     |     |     |     | 215 |     |     |     | 220 |     |     |     |     |     |     |

( 2 ) INFORMATION FOR SEQ ID NO:4:

( i ) SEQUENCE CHARACTERISTICS:
        ( A ) LENGTH: 219 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Cys | Pro | Ala | Arg | Ser | Leu | Leu | Leu | Val | Ala | Thr | Leu | Val | Leu | Leu |
| --- | --- | --- | --- | --- | --- | --- | --- | --- | --- | --- | --- | --- | --- | --- | --- |
| 1 |     |     |     | 5 |     |     |     |     | 10 |     |     |     |     | 15 |     |
| Asp | His | Leu | Ser | Leu | Ala | Arg | Asn | Leu | Pro | Val | Ala | Thr | Pro | Asp | Pro |
|     |     |     | 20 |     |     |     |     | 25 |     |     |     | 30 |     |     |     |
| Gly | Met | Phe | Pro | Cys | Leu | His | His | Ser | Gln | Asn | Leu | Leu | Arg | Ala | Val |
|     |     | 35 |     |     |     |     | 40 |     |     |     |     | 45 |     |     |     |
| Ser | Asn | Met | Leu | Gln | Lys | Ala | Arg | Gln | Thr | Leu | Glu | Phe | Tyr | Pro | Cys |
|     | 50 |     |     |     |     | 55 |     |     |     |     | 60 |     |     |     |     |
| Thr | Ser | Glu | Glu | Ile | Asp | His | Glu | Asp | Ile | Thr | Lys | Asp | Lys | Thr | Ser |
| 65 |     |     |     |     | 70 |     |     |     |     | 75 |     |     |     |     | 80 |
| Thr | Val | Glu | Ala | Cys | Leu | Pro | Leu | Glu | Leu | Thr | Lys | Asn | Glu | Ser | Cys |
|     |     |     |     | 85 |     |     |     |     | 90 |     |     |     |     | 95 |     |
| Leu | Asn | Ser | Arg | Glu | Thr | Ser | Phe | Ile | Thr | Asn | Gly | Ser | Cys | Leu | Ala |
|     |     |     | 100 |     |     |     |     | 105 |     |     |     |     | 110 |     |     |
| Ser | Arg | Lys | Thr | Ser | Phe | Met | Met | Ala | Leu | Cys | Leu | Ser | Ser | Ile | Tyr |
|     |     | 115 |     |     |     |     | 120 |     |     |     |     | 125 |     |     |     |
| Glu | Asp | Leu | Lys | Met | Tyr | Gln | Val | Glu | Phe | Lys | Thr | Met | Asn | Ala | Lys |
|     | 130 |     |     |     |     | 135 |     |     |     |     | 140 |     |     |     |     |
| Leu | Leu | Met | Asp | Pro | Lys | Arg | Gln | Ile | Phe | Leu | Asp | Gln | Asn | Met | Leu |
| 145 |     |     |     |     | 150 |     |     |     |     | 155 |     |     |     |     | 160 |
| Ala | Val | Ile | Asp | Glu | Leu | Met | Gln | Ala | Leu | Asn | Phe | Asn | Ser | Glu | Thr |
|     |     |     |     | 165 |     |     |     |     | 170 |     |     |     |     | 175 |     |
| Val | Pro | Gln | Lys | Ser | Ser | Leu | Glu | Glu | Pro | Asp | Phe | Tyr | Lys | Thr | Lys |
|     |     |     | 180 |     |     |     |     | 185 |     |     |     |     | 190 |     |     |
| Ile | Lys | Leu | Cys | Ile | Leu | Leu | His | Ala | Phe | Arg | Ile | Arg | Ala | Val | Thr |
|     |     | 195 |     |     |     |     | 200 |     |     |     |     | 205 |     |     |     |
| Ile | Asp | Arg | Val | Met | Ser | Tyr | Leu | Asn | Ala | Ser |     |     |     |     |     |
|     | 210 |     |     |     |     | 215 |     |     |     |     |     |     |     |     |     |